(12) United States Patent
Maeda et al.

(10) Patent No.: US 8,550,711 B2
(45) Date of Patent: Oct. 8, 2013

(54) TREATMENT TABLE SYSTEM

(75) Inventors: Hironori Maeda, Tokyo (JP); Hiroshi Otani, Tokyo (JP)

(73) Assignee: Mitsubishi Electric Corporation, Chiyoda-Ku, Tokyo (JP)

(*) Notice: Subject to any disclaimer, the term of this patent is extended or adjusted under 35 U.S.C. 154(b) by 274 days.

(21) Appl. No.: 12/997,727

(22) PCT Filed: Jun. 18, 2008

(86) PCT No.: PCT/JP2008/001574
§ 371 (c)(1),
(2), (4) Date: Feb. 8, 2011

(87) PCT Pub. No.: WO2009/153832
PCT Pub. Date: Dec. 23, 2009

(65) Prior Publication Data
US 2011/0121197 A1    May 26, 2011

(51) Int. Cl.
*A61B 6/04* (2006.01)
(52) U.S. Cl.
USPC ............. 378/209; 378/20; 378/68; 378/69; 378/208; 250/492.1
(58) Field of Classification Search
USPC ............ 378/20, 68, 69, 208, 209; 250/492.1, 250/492.3
See application file for complete search history.

(56) References Cited

U.S. PATENT DOCUMENTS

| 5,329,567 A | 7/1994 | Ikebe |
| 5,615,430 A | 4/1997 | Nambu et al. |
| 6,094,760 A * | 8/2000 | Nonaka et al. ............. 5/601 |
| 2004/0034438 A1 | 2/2004 | Uematsu |
| 2004/0131150 A1 | 7/2004 | Pankrtov et al. |

FOREIGN PATENT DOCUMENTS

| JP | 5-309091 A | 11/1993 |
| JP | 8-038628 A | 2/1996 |
| JP | 8-057069 A | 3/1996 |
| JP | 11-009708 A | 1/1999 |
| JP | 11-313900 A | 11/1999 |
| JP | 2001-299943 A | 10/2001 |
| JP | 2004-255160 A | 9/2004 |
| JP | 2005-052308 A | 3/2005 |
| JP | 2007-195877 A | 8/2007 |

OTHER PUBLICATIONS

Translation for JP 2001-29943 A published on Oct. 30, 2001.*

(Continued)

*Primary Examiner* — Glen Kao
(74) *Attorney, Agent, or Firm* — Buchanan Ingersoll & Rooney PC

(57) ABSTRACT

Lesion positioner systems and, which perform positioning of a lesion A by moving a top board for allowing a subject to be placed thereon, set an isocenter of a diagnostic 3D imaging unit as a virtual isocenter at the time when a treatment table is in a 3D imaging diagnosis position, and positions the lesion A to the virtual isocenter, based on a three-dimensional diagnostic image in consideration of particle beam therapy. A treatment table moving mechanism moves the treatment table to the treatment position relative to the particle beam therapy system while maintaining states of the top board and the lesion positioner systems and at the time of positioning, thereby positioning the lesion A to the isocenter of the particle beam therapy system.

3 Claims, 10 Drawing Sheets

(56) References Cited

OTHER PUBLICATIONS

Translation for JP 2007-195877 A published on Aug. 9, 2007.*
Office Action issued on Aug. 3, 2010, by Japanese Patent Office for Application No. 2010-517549.
International Search Report (PCT/ISA/210) issued on Sep. 9, 2008, by Japanese Patent Office as the International Searching Authority for International Application No. PCT/JP2008/001574.
Chinese Office Action issued from the Chinese Patent Office on Apr. 23, 2013 in corresponding Chinese Patent Application No. 200880129958.3 with partial English translation.

* cited by examiner (a) Three-dimensional diagnosis (b) Particle beam treatment

TREATMENT TABLE SYSTEM

TECHNICAL FIELD

The present invention relates to a treatment table system used for a particle beam therapy system, and particularly relates to a treatment table system for facilitating employment of diagnosis by a diagnostic 3D imaging unit for particle beam therapy.

BACKGROUND ART

Conventional radiation therapy using X-rays or gamma rays, which is a widely used treatment method, provides a high dose of radiation to a human body regardless of the depth from the skin surface, and thus the radiation affects normal cells before it reaches a lesion. On the other hand, particle beam therapy which uses proton beams or heavy charged particle beam is characterized in that a dose of the particle radiation reaches its peak at a predetermined depth from the skin surface of a human body, and thus enables intensive irradiation of a lesion while minimizing damages of normal cells, which is an effective treatment method.

However, a particle beam therapy system is a large-size apparatus that irradiates a lesion with high energy charged particle beams emitted from a large-size accelerator. Thus, the arrangement of equipment relating to the beam delivery system is determined uniquely, and a radiation port including a radiation aperture for emitting particle beams cannot be arranged arbitrarily.

A diagnostic 3D imaging unit, which is typified by a CT device, is preferably used for diagnosis of positioning of a lesion having a three-dimensional shape. However, it is difficult to arrange the particle radiation port so as not to interfere with the large-size diagnostic 3D imaging unit. Accordingly, in order to employ diagnosis by the diagnostic 3D imaging unit for the particle beam therapy, the following procedure has been necessary: a lesion is positioned in a treatment table of the diagnostic 3D imaging unit; a treatment plan is prepared based on the positioning; a subject is moved to a treatment table of the particle beam therapy system; the lesion is positioned again; and treatment is then performed. Thus, the positioning accuracy has been low.

Described below is an example of a conventional treatment table (couch) system which enables positioning using a common couch without requiring a subject to move between different treatment tables of a plurality of apparatuses such as a diagnostic apparatus and a treatment apparatus.

This system is provided with a couch used in common for a plurality of medical apparatuses, means for supporting the couch so as to be moved in one direction of three-dimensional directions, and means for controlling the movement of the couch in the one direction thereby to individually position a subject to an isocenter of each of the plurality of medical apparatuses. The positions of the respective isocenters of the plurality of medical apparatuses, with respect to the remaining two directions of the three-dimensional directions, are set identical to one another (see Patent Document 1, for example).

[Patent Document 1] Japanese Laid-Open Patent Publication No. 2005-52308

DISCLOSURE OF THE INVENTION

Problems to be Solved by the Invention

In the treatment table system disclosed in above Patent Document 1, after a lesion is positioned to the isocenter of a diagnostic 3D imaging unit or the like, the treatment table is moved with a simple operation, and then the lesion is positioned to the isocenter of a treatment apparatus. However, to position the lesion to the isocenters, positioning of a radiation port in the treatment apparatus is required in addition to the positioning based on the treatment table. Thus, the system cannot be applied to such a particle beam therapy system in which the position of the radiation port is fixed.

The present invention is made to solve the above problem, and is intended to provide a treatment table system which employs diagnosis by a diagnostic 3D imaging unit for particle beam therapy and allows easy and highly accurate positioning of a lesion relative to isocenters.

Solution to the Problems

A treatment table system according to the present invention is a treatment table system for a particle beam therapy system which employs 3D imaging diagnosis for particle beam therapy in which a lesion of a subject is irradiated with high energy charged particle beams emitted from an accelerator. The treatment table system includes: a top board on which the subject is placed; a lesion positioner system which supports and moves the top board thereby to position the lesion to an isocenter of the particle beam therapy system; and a treatment table moving mechanism which moves a treatment table provided with the lesion positioner system and the top board between a diagnosis position in a diagnostic 3D imaging unit and a treatment position relative to the particle beam therapy system. When the treatment table is in the diagnosis position in the diagnostic 3D imaging unit, the lesion positioner system sets an isocenter of the diagnostic 3D imaging unit as a virtual isocenter of the particle beam therapy system, and positions the lesion to the virtual isocenter, based on an image of the lesion obtained by the diagnostic 3D imaging unit, in consideration of particle beam therapy based on a position of a particle radiation port and a direction of particle radiation in the particle beam therapy system. The treatment table moving mechanism moves the treatment table to the treatment position relative to the particle beam therapy system while maintaining states of the top board and the lesion positioner system at a time of positioning when the lesion is positioned to the virtual isocenter, thereby to position the lesion to the isocenter of the particle beam therapy system.

Effect of the Invention

The treatment table system according to the present invention employs a treatment table for both the 3D imaging diagnosis and the particle beam therapy, and allows positioning of a lesion to an isocenter of the particle beam therapy system easily and highly accurately only by moving the treatment table to the patient position of particle beam therapy while maintaining the state of the positioned lesion based on a result of diagnosis by the diagnostic 3D imaging unit.

BEST MODE FOR CARRYING OUT THE INVENTION

Embodiment 1

Figure 1:
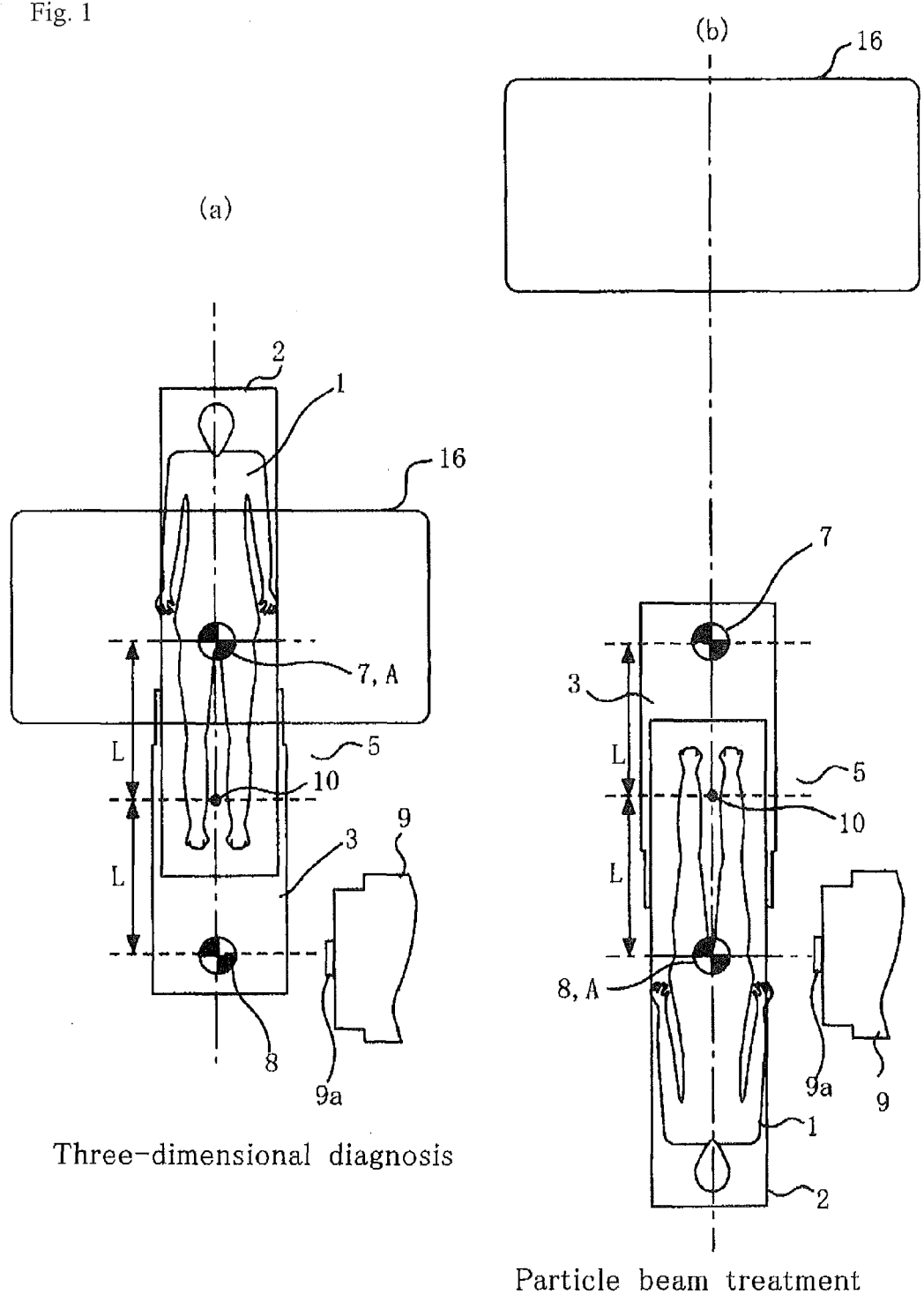
FIG. 1 is a diagram illustrating a schematic structure of a treatment table system according to Embodiment 1 of the present invention, used for a 3D imaging diagnosis and for particle beam therapy.
Figure 2:
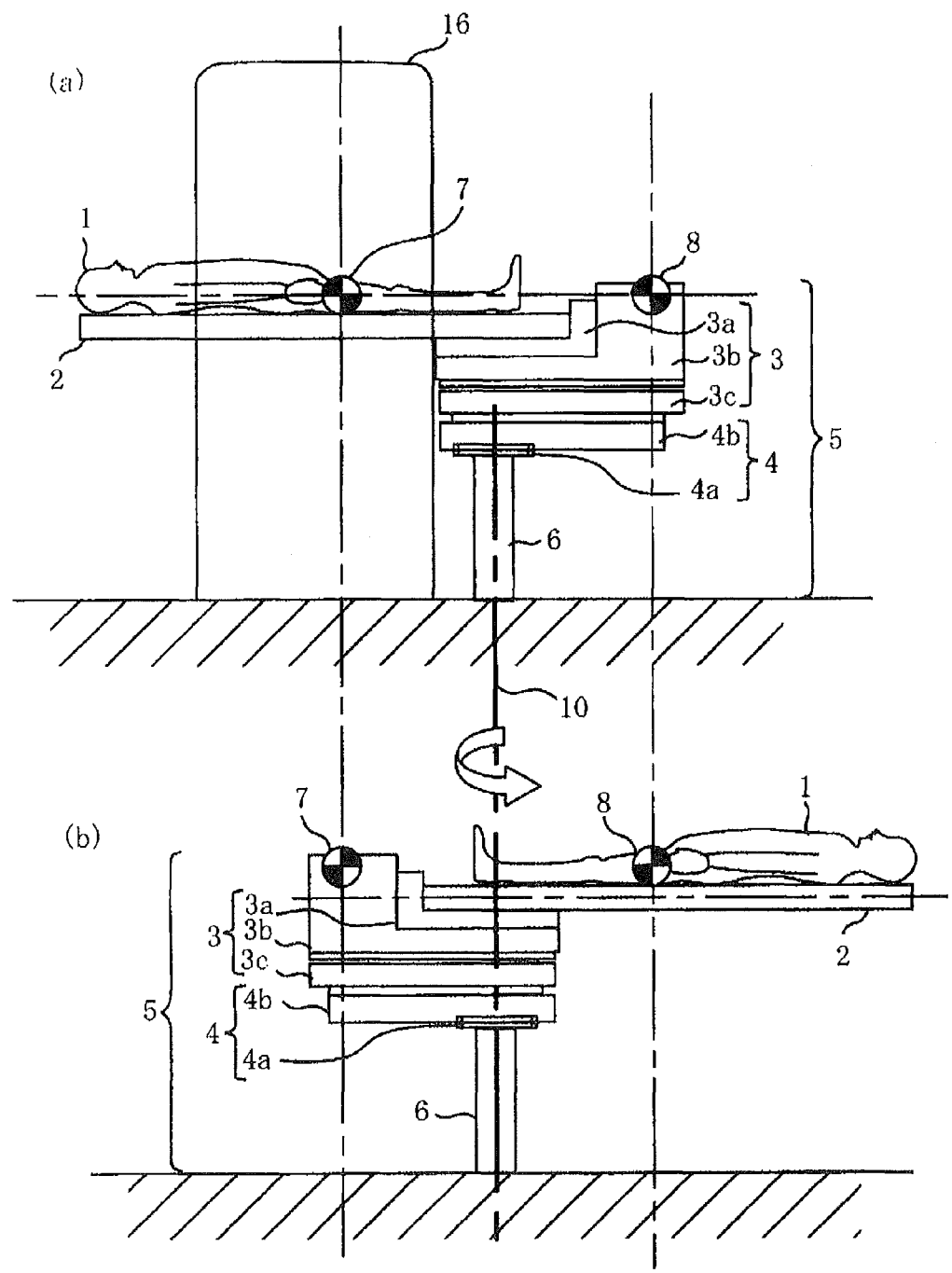
FIG. 2 is a diagram illustrating a lesion positioner system of the treatment table system according to Embodiment 1 of the present invention.

Hereinafter, a treatment table system according to Embodiment 1 of the present invention will be described with reference to drawings. FIG. 1(a) and FIG. 1(b) are each a top view illustrating a schematic structure of the treatment table system according to Embodiment 1 of the present invention. In addition, FIG. 2(a) and FIG. 2(b) each illustrate a side view of the treatment table system illustrated in FIG. 1(a) and FIG. 1(b). Particularly, FIG. 1(a) and FIG. 2(a) each illustrate a treatment table 5 arranged in a 3D imaging diagnosis position, whereas FIG. 1(b) and FIG. 2(b) each illustrate the treatment table 5 arranged in a patient position of particle beam therapy.

As shown in the drawings, the treatment table system includes a treatment table 5 which is provided with: a top board 2 on which a patient 1, i.e., a subject is placed; a first lesion positioner system 3 and a second lesion positioner system 6 which support the top board 2 and move the top board 2 for positioning the lesion A; and a treatment table moving mechanism 4 arranged under the first lesion positioner system 3. Further, the system includes a control unit (not shown) which controls the first and second lesion positioner systems 3 and 6, and the treatment table moving mechanism 4.

The first lesion positioner system 3 is formed of a plurality of members 3a to 3c. The first lesion positioner system 3 supports the top board 2, and also moves the top board 2, based on a combination of any of movements in a longitudinal direction, in a lateral direction, in a rotation direction about an axis along the longitudinal direction, and in a rotation direction about an axis along the lateral direction, thereby to position the lesion A relative to the directions other than a vertical direction. The second lesion positioner system 6 is configured with a support leg 6. The support leg 6 moves the top board 2 in the vertical direction by expanding and contracting vertically, thereby to position the lesion A relative to the vertical direction.

The treatment table moving mechanism 4 moves the treatment table 5 between a diagnosis position in the diagnostic 3D imaging unit 16 and a treatment position relative to the particle beam therapy system, and is driven independently from the first and second lesion positioner systems 3 and 6. The treatment table moving mechanism 4 is configured with a turntable 4a, and a seat 4b which is arranged on the turntable 4a thereby to rotate integrally with the turntable 4a. The treatment table moving mechanism 4 is arranged under the first lesion positioner system 3 to support the first lesion positioner system 3. The treatment table moving mechanism 4, the first lesion positioner system 3, and the top board 2 are rotated integrally, whereby the treatment table 5 is moved.

As shown in FIG. 1(a) and FIG. 2(a), when the treatment table 5 is in the diagnosis position in the diagnostic 3D imaging unit 16, an isocenter of the diagnostic 3D imaging unit 16 is set as a virtual isocenter 7 of the particle beam therapy system, and the lesion A is positioned to the virtual isocenter 7 by the first and second lesion positioner systems 3 and 6. In this case, the diagnostic 3D imaging unit 16 is arranged in a position that keeps the apparatus 16 from interfering with a radiation port 9 including a particle radiation aperture 9a of the particle beam therapy system.

Positioning of the lesion A to the virtual isocenter 7 is performed in consideration of the particle beam therapy, and thus corresponds to an operation of positioning, necessary for particle beam therapy, to the isocenter 8 of the actual particle beam therapy system. Thus, in consideration of the particle beam therapy based on the position of the particle radiation aperture 9a which is fixed, and on the direction of particle radiation, the top board 2 is moved by using any of the movements in the longitudinal direction, in the lateral direction, and in the vertical direction, and in addition using a roll angle adjustment for a movement in the rotation direction about the longitudinal direction axis, and a pitch angle adjustment for a movement in the rotation direction about the lateral direction axis, whereby the lesion A is positioned. The virtual isocenter 7 is the isocenter of the diagnostic 3D imaging unit 16, and is thus positioned based on a three-dimensional diagnostic image taken by the diagnostic 3D imaging unit 16, which allows highly accurate positioning based on the three-dimensional shape of the lesion A.

Figure 3:
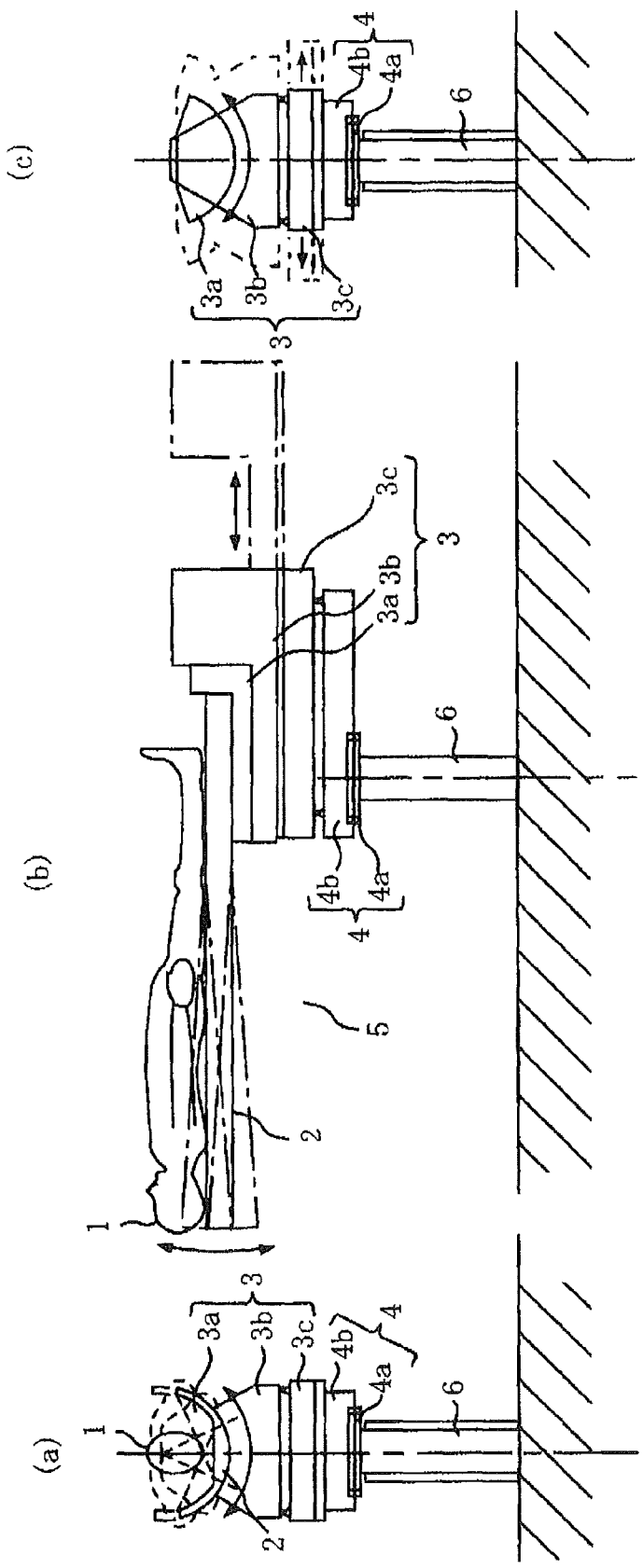
FIG. 3 is a side view of the treatment table system illustrated in FIG. 1.

FIG. 3(a), FIG. 3(b), and FIG. 3(c) are side views from three directions, each illustrating an operation by the first lesion positioner system 3.

The member 3a of the first lesion positioner system 3 performs the roll angle adjustment (see FIG. 3(a)) and the pitch angle adjustment (see FIG. 3(b)) to the top board 2. The member 3b moves the top board 2 together with the member 3a in the longitudinal direction (see FIG. 3(b)), and the member 3c moves the top board 2 together with the members 3a and 3b in the lateral direction (see FIG. 3(c)).

The treatment table moving mechanism 4 moves the treatment table 5 to the treatment position relative to the particle beam therapy system while maintaining the state of the top board 2, and the first and second lesion positioner systems 3 and 6 obtained at the time when the lesion A is positioned to the virtual isocenter 7, whereby the state illustrated in FIG. 1(b) and FIG. 2(b) is obtained. That is, the lesion A positioned to the virtual isocenter 7 is moved and positioned to the isocenter 8 in the particle beam therapy system. In this case, the treatment table 5 is rotated by 180 degrees about a rotation axis 10 which passes through a midway point between the virtual isocenter 7 and the isocenter 8. The center of the turntable 4a is located on the rotation axis 10. Note that the support leg 6 arranged under the turntable 4a does not rotate but is fixed, and has a symmetric shape relative to the rotation axis 10.

When the treatment table 5 is to be moved, the diagnostic 3D imaging unit 16 is removed backward so as not to hinder the movement of the treatment table 5. Note that in FIG. 1(*a*) and FIG. 1(*b*), the radiation port 9 is located close to the treatment table 5 for convenience. However, the radiation port 9 is fixed to a wall surface of the treatment room so as not to hinder the rotation of the treatment table 6.

After the lesion A is positioned to the isocenter 8 of the particle beam therapy system, the particle beam therapy system emits particle beams from the particle radiation aperture 9*a* thereby irradiating and treating the lesion A with the beams.

Figure 4:
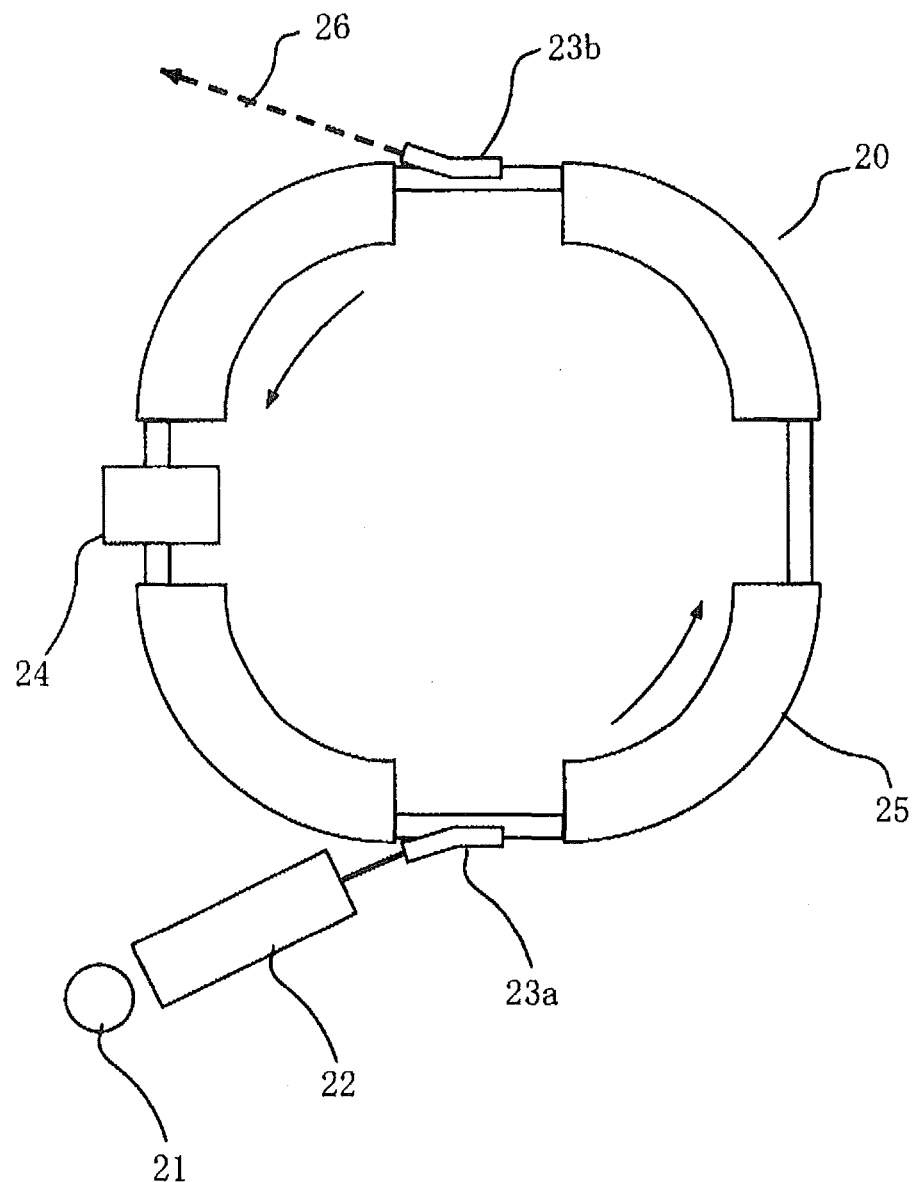
FIG. 4 is a diagram illustrating a structure of an accelerator used for the particle beam therapy according to Embodiment 1 of the present invention.

The particle beam therapy apparatus is provided with: a large-size accelerator 20; a transport system which introduces charged particle beams emitted from the accelerator 20 into a treatment room; and a beam delivery system which appropriately irradiates the lesion A with the particle beams which are the charged particle beams having been supplied, and the particle beams are emitted from the radiation aperture 9*a*. FIG. 4 is a diagram illustrating a schematic structure of the accelerator 20. As shown in the diagram, accelerated particles are outputted, as the charged particle beams, from an ion source 21, and are accelerated to a certain level of energy by a linear accelerator 22. Such accelerated beams are inputted from an injector 23*a* to a circular trajectory. The charged particle beams pass through an acceleration cavity 24 each time they travel along the circular trajectory, and are accordingly accelerated, and thereby the energy is increased. Along with the acceleration, the magnetic field is increased so that the charged particle beams travel along the same circular trajectory. When the charged particle beams have reached a maximum energy level, the charged particle beams are outputted to the outside of the circular trajectory from a beam extraction system 23*b*.

In this embodiment, when the treatment table 5 is in the diagnosis position in the diagnostic 3D imaging unit 16, the first and second lesion positioner systems 3 and 6 set the isocenter of the diagnostic 3D imaging unit 16 as the virtual isocenter 7 of the particle beam therapy system in consideration of the particle beam therapy, and position the lesion A to the virtual isocenter 7, based on an image of the lesion A obtained by the diagnostic 3D imaging unit 16. The positioning is not only based on any of the movements in the longitudinal direction, in the lateral direction, and in the vertical direction, but also based on the roll angle adjustment which is the rotational movement about the axis along the longitudinal direction and on the pitch angle adjustment which is the rotational movement about the axis along the lateral direction.

In a usual 3D imaging diagnosis, when the lesion is positioned to the isocenter of the diagnostic 3D imaging unit, it is unnecessary to perform the roll angle adjustment which is the rotational movement about the axis along the longitudinal direction and the pitch angle adjustment which is the rotational movement about the axis along the lateral direction to a couch where a subject is placed. The couch in the diagnostic 3D imaging unit does not have such a positioner system.

In the treatment table system according to this embodiment, the lesion A is positioned to the virtual isocenter 7 in consideration of the particle beam therapy with a particle beam therapy system in which the position of the radiation port 9 is not adjustable. Accordingly, it is possible to perform positioning, necessary for the actual particle beam therapy, to the isocenter 8 of the particle beam therapy system. In addition, the positioning is performed based on a diagnostic image obtained through the 3D imaging diagnosis by the diagnostic 3D imaging unit 16, and thus the positioning can be performed highly accurately based on the three-dimensional shape of the lesion A. Further, it is possible to locate the diagnostic 3D imaging unit 16 in a manner as not to interfere with the radiation port 9 of the particle beam therapy system, and thus can be applied to existing particle beam therapy systems thereby to position the lesion A to the virtual isocenter 7.

Moreover, the treatment table moving mechanism 4 moves the treatment table 5 to the treatment position relative to the particle beam therapy system, while maintaining the states of the top board 2, and the first and second lesion positioner systems 3 and 6 obtained at the time when the lesion A is positioned to the virtual isocenter 7. The treatment table moving mechanism 4 is driven independently from the first and second lesion positioner systems 3 and 6, and thus the states of the top board 2, and the first and second lesion positioner systems 3 and 6 can be maintained when the treatment table 5 is moved by the treatment table moving mechanism 4. Accordingly, it is possible to maintain the accuracy in positioning the treatment table 5 between the diagnosis position and the treatment position, and also possible to prevent changes in the states, such as deflection and deformation, of the top board 2, and the first and second lesion positioner systems 3 and 6 when they are in the diagnosis position, in the treatment position, and even being moved from the diagnosis position to the treatment position. Therefore, it is possible to prevent a change in a body posture of the subject 1 or a movement of the organs, and the lesion A can be positioned to the isocenter 8 of the particle beam therapy system highly accurately. Note that the support leg 6, which is the second lesion positioner system 6, does not rotate. The support leg 6 has a symmetric shape relative to the rotation axis 10, which can prevent the changes in the state such as deflection and deformation between the diagnosis position and the treatment position.

With only a rotational movement of the treatment table 5 by 180 degrees on a two-dimensional plane, the lesion A positioned at the virtual isocenter 7 is moved to the position of the isocenter 8 of the particle beam therapy system. That is, the treatment table 5 can be moved easily and simply, and in addition, the change in the body posture of the subject 1 or movement of the organs can be further effectively prevented. Moreover, the shape of the treatment table moving mechanism 4 and its relative position in the treatment table 5 will not change between the diagnosis position and the treatment position, and accordingly, no change in the state such as deflection or deformation of the entire treatment table 5 occurs between the diagnosis position and the treatment position. Thus, the lesion A can be further highly accurately positioned to the isocenter 8 of the particle beam therapy system.

Note that, in the above embodiment, the isocenter of the diagnostic 3D imaging unit 16 is set as the virtual isocenter 7 of the particle beam therapy system. However, since the diagnostic 3D imaging unit 16 is movable, the virtual isocenter 7 may be set within the diagnostic coverage of the diagnostic 3D imaging unit 16, and the diagnostic 3D imaging unit 16 may be moved so that the isocenter of the diagnostic 3D imaging unit 16 coincides with the virtual isocenter 7.

In this case, under a state where the treatment table 5 is arranged in the treatment position relative to the particle beam therapy system, the positional information of the isocenter 8 is recorded optically by using a laser pointer, or mechanically or electronically by using position sensors provided to the first and second lesion positioner systems 3 and 6, for example. The treatment table 5 is then arranged near the diagnostic 3D imaging unit 16 by using the treatment table moving mechanism 4, and the virtual isocenter 7 is set within the diagnostic coverage of the diagnostic 3D imaging unit 16, based on the above recorded positional information of the isocenter 8. In this case, the virtual isocenter 7 is set such that the isocenter 8 and the virtual isocenter 7 are symmetric about the rotation axis 10 of the treatment table 5.

Embodiment 2

Hereinafter, a treatment table system according to Embodiment 2 of the present invention will be described with reference to FIG. 5 to FIG. 8.

The treatment table moving mechanism 4 of this Embodiment 2 is different from that of above Embodiment 1. Meanwhile, the top board 2 and the first lesion positioner system 3 are the same as those of above Embodiment 1. The first lesion positioner system 3 not only supports the top board 2, but also moves the top board 2, based on a combination of any of the movements in the longitudinal direction and in the lateral direction, the rotational movement about the axis along the longitudinal direction, and the rotational movement about the axis along the lateral direction, thereby positioning the lesion A relative to the directions other than the vertical direction. Note that the top board 2 and the first lesion positioner system 3 are illustrated simply for convenience.

The second lesion positioner system 6*a* formed of a support leg 6*a* is the same as that of above Embodiment 1 in that it expands and contracts vertically, thereby to move the top board 2 in the vertical direction. However, the width of the mechanism 6*a* is wider than that of Embodiment 1.

The treatment table moving mechanism 4 is located under the first lesion positioner system 3 and supports the first lesion positioner system 3. The mechanism 4 is driven independently from the first and second lesion positioner systems 3 and 6*a*. The mechanism 4 then moves the treatment table 5, while maintaining the states of the top board 2 and the first and second lesion positioner systems 3 and 6*a* obtained at the time when the lesion A is positioned to the virtual isocenter 7, between the diagnosis position in the diagnostic 3D imaging unit 16 and the treatment position relative to the particle beam therapy system.

Figure 5:
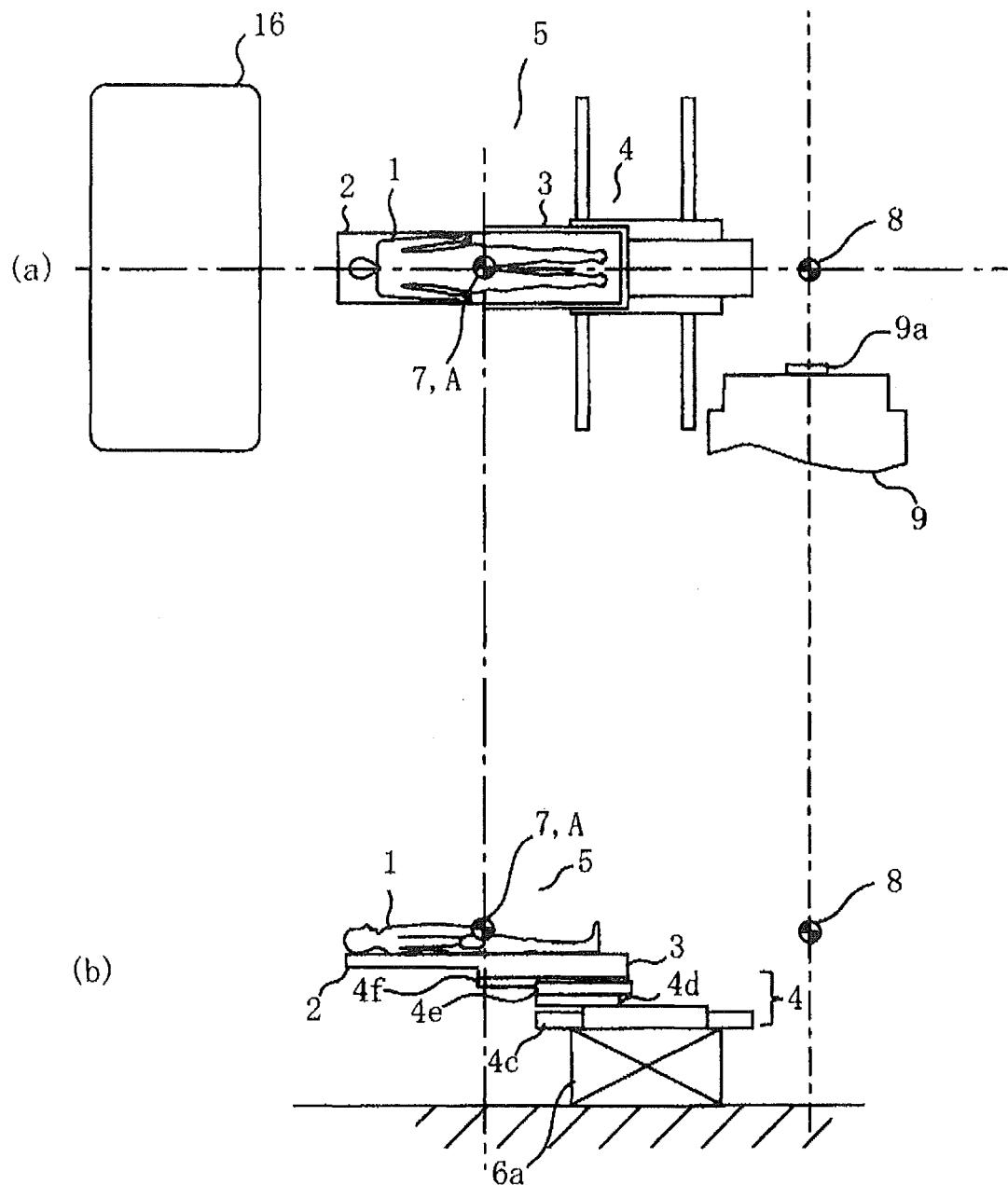
FIG. 5 is a diagram illustrating a structure and operation of a treatment table moving mechanism of a treatment table system according to Embodiment 2 of the present invention.
Figure 7:
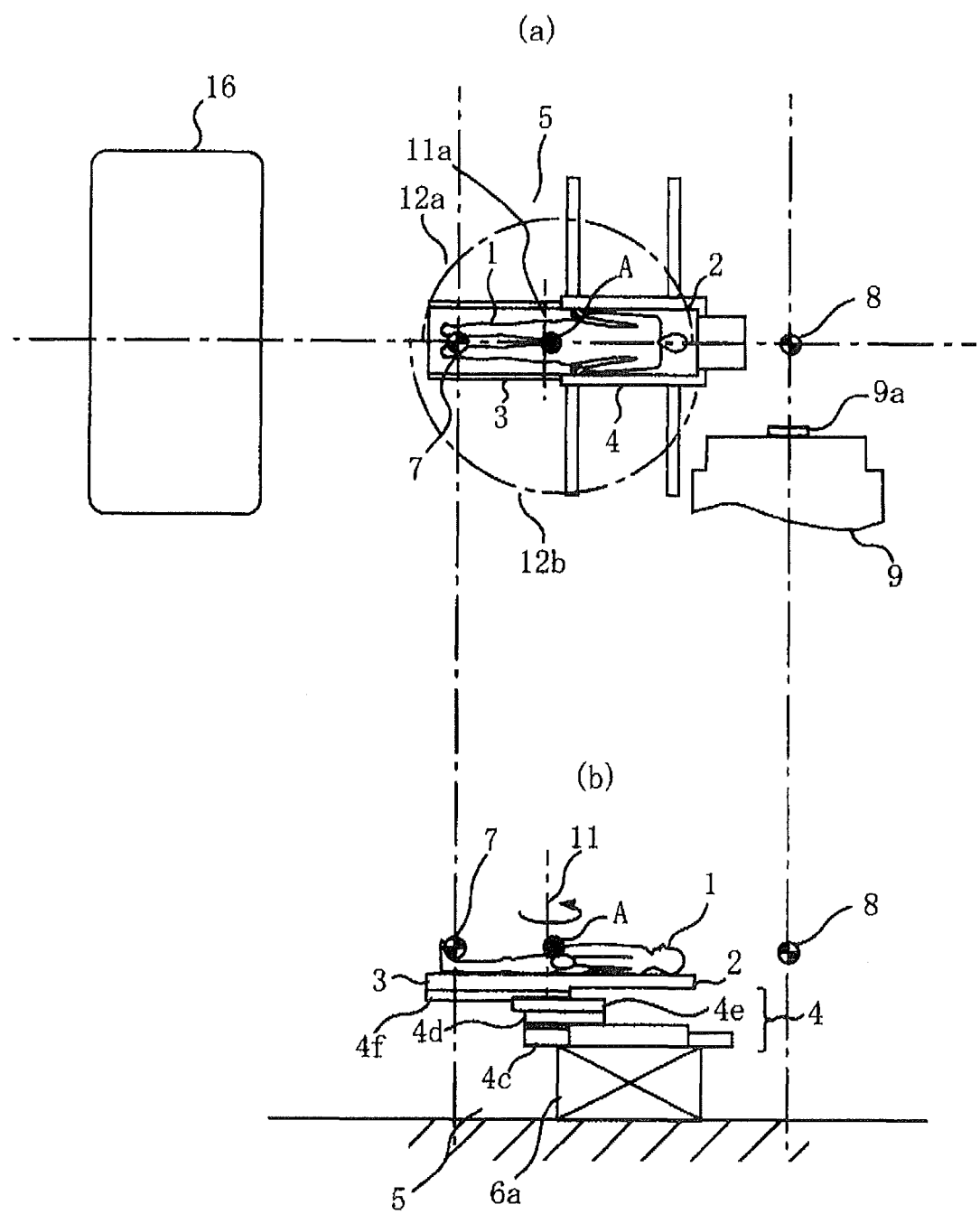
FIG. 7 is a diagram illustrating a structure and operation of the treatment table moving mechanism of the treatment table system according to Embodiment 2 of the present invention.
Figure 8:
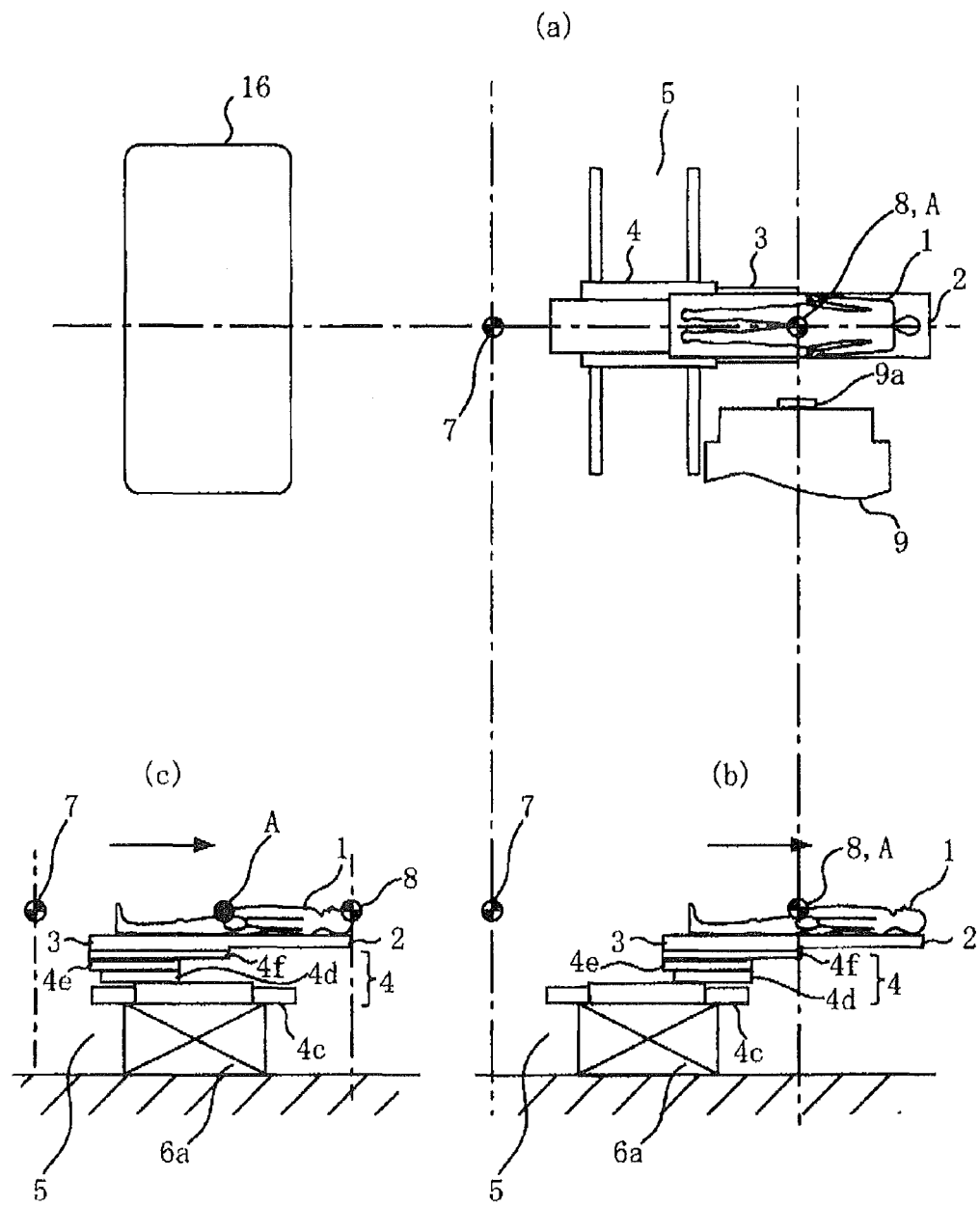
FIG. 8 is a diagram illustrating a structure and operation of the treatment table moving mechanism of the treatment table system according to Embodiment 2 of the present invention.

Note that FIG. 5(*a*) and FIG. 5(*b*) are each a diagram illustrating the treatment table 5 arranged in the 3D imaging diagnosis position, whereas FIG. 8(*a*) and FIG. 8(*b*) are each a diagram illustrating the treatment table 5 arranged in the patient position of particle beam therapy. In addition, FIG. 6(*a*), FIG. 6(*b*), FIG. 7(*a*), FIG. 7(*b*), and FIG. 8(*c*) each illustrate a step of a procedure of moving the treatment table 5 from the 3D imaging diagnosis position to the patient position of particle beam therapy. Note that FIG. 5(*a*), FIG. 6(*a*), FIG. 7(*a*), and FIG. 8(*a*) are each a top view, and FIG. 5(*b*), FIG. 6(*b*), FIG. 7(*b*), and FIG. 8(*b*) are each a side view.

As shown in the drawings, the treatment table moving mechanism 4 is configured such that Members 4*c* to 4*f* are arranged hierarchically in the height direction. Note that the member 4*c* is arranged on the support leg 6*a* so as to support the members 4*d* to 4*f* thereon, and does not move itself.

As shown in FIG. 5(*a*) and FIG. 5(*b*), when the treatment table 5 is in the diagnosis position in the diagnostic 3D imaging unit 16, the isocenter of the diagnostic 3D imaging unit 16 is set as the virtual isocenter 7 of the particle beam therapy system, and the lesion A is positioned to the virtual isocenter 7 by using the first and second lesion positioner systems 3 and 6*a*. The drawings illustrate the state where after the lesion A is positioned to the virtual isocenter 7, the diagnostic 3D imaging unit 16 is removed backward to facilitate the movement of the treatment table 5.

Figure 6:
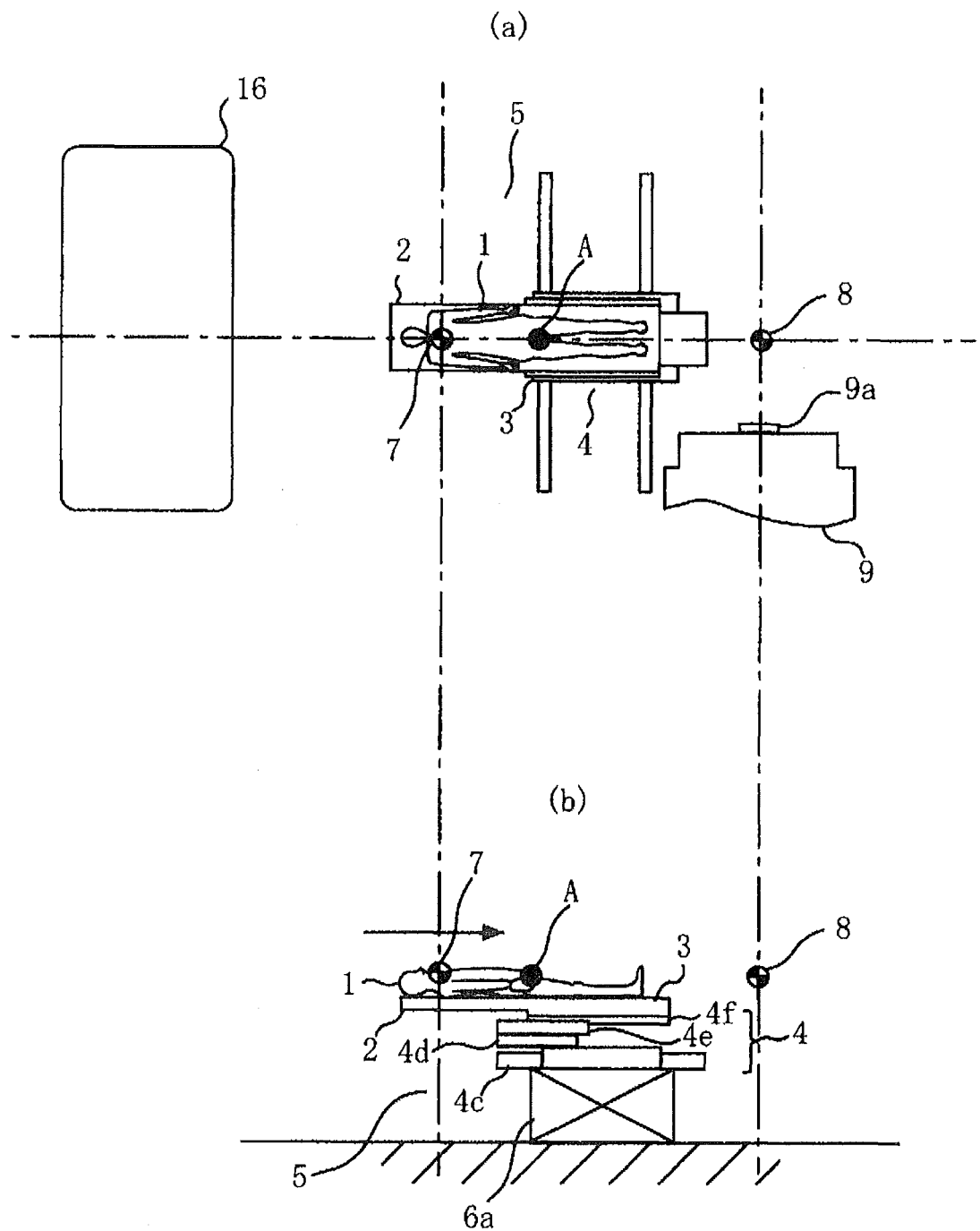
FIG. 6 is a diagram illustrating a structure and operation of the treatment table moving mechanism of the treatment table system according to Embodiment 2 of the present invention.

The treatment table moving mechanism 4 moves the treatment table 5 as shown in FIG. 6(*a*) and FIG. 6(*b*) while maintaining the states of the top board 2 and the first and second lesion positioner systems 3 and 6*a* obtained at the time when the lesion A is positioned to the virtual isocenter 7. In this case, the member 4*f* of the treatment table moving mechanism 4, arranged under the bottom surface of the first lesion positioner system 3, moves the top board 2 and the first lesion positioner system 3 integrally to the right in the drawings. As a result, the dimension of the entire treatment table 5 in the longitudinal direction is reduced. Note that the member 4*f* may be attached to the upper surface of the member 4*e* placed therebelow, and in this case, the top board 2 and the first lesion positioner system 3 may be moved integrally by driving the member 4*f*.

Next, the treatment table moving mechanism 4 further moves the treatment table 5 as shown in FIG. 7(*a*) and FIG. 7(*b*) while maintaining the states of the top board 2, and the first and second lesion positioner systems 3 and 6*a* obtained at the time when the lesion A is positioned to the virtual isocenter 7. In this case, the member 4*e* of the treatment table moving mechanism 4 is rotationally driven, and the top board 2, the first lesion positioner system 3, and the members 4*f* and 4*e* are integrally rotated by 180 degrees about the rotation axis 11. This rotational movement can be performed without interfering with the radiation port 9, since the dimension of the treatment table 5 in the longitudinal direction is reduced in the preceding step and consequently the radius of the rotation decreases.

Next, the treatment table moving mechanism 4 further moves the treatment table 5 as shown in FIG. 8(*c*) while maintaining the states of the top board 2 and the first and second lesion positioner systems 3 and 6*a* obtained at the time when the lesion A is positioned to the virtual isocenter 7. In this case, the member 4*f* of the treatment table moving mechanism 4, arranged under the bottom surface of the first lesion positioner system 3, moves the top board 2 and the first lesion positioner system 3 integrally to the right in the drawing. The movement is relatively equal to a movement of turning back the movement shown in FIG. 6(*a*) and FIG. 6(*b*).

Next, the treatment table moving mechanism 4 further moves the treatment table 5 as shown in FIG. 8(*a*) and FIG. 8(*b*) while maintaining the states of the top board 2, the first and second lesion positioner systems 3 and 6*a* obtained at the time when the lesion A is positioned to the virtual isocenter 7. In this case, the member 4*d* of the treatment table moving mechanism 4 moves the top board 2, the first lesion positioner system 3, and the members 4*f* and 4*e* integrally to the right in the drawing. The lesion A is then moved and positioned to the isocenter 8 of the particle beam therapy system.

In this embodiment, the respective members 4*d* to 4*f* of the treatment table moving mechanism 4 are driven successively by respectively independent driving mechanisms, and change the overall shape of the treatment table 5 while the treatment table 5 is being moved from the 3D imaging diagnosis position to the patient position of particle beam therapy. The shape and the relative position, in the treatment table 5, of the treatment table moving mechanism 4 at the time when the treatment table 5 has reached the patient position of particle beam therapy, i.e., when the lesion A is moved to the position of the isocenter 8 of the particle beam therapy system, are the same as those at the time when the lesion A is positioned to the virtual isocenter 7. Accordingly, the radius of rotation can be reduced at the time of the rotational movement as described above, for example. Thus, the degree of freedom of movement can be increased, and consequently the degree of freedom in designing can be improved.

In a similar manner as above Embodiment 1, the treatment table moving mechanism 4 moves the treatment table 5 to the treatment position relative to the particle beam therapy system while maintaining the states of the top board 2 and the first and second lesion positioner systems 3 and 6a obtained at the time when the lesion A is positioned to the virtual isocenter 7. The treatment table moving mechanism 4 is driven independently from the first and second lesion positioner systems 3 and 6a, and thus when the treatment table moving mechanism 4 moves the treatment table 5, the states of the top board 2 and the first and second lesion positioner systems 3 and 6a can be maintained. Accordingly, it is possible to maintain accuracy in positioning the treatment table 5 between the diagnosis position and the treatment position, and also possible to prevent changes in the states such as deflection and deformation of the top board 2, and the first and second lesion positioner systems 3 and 6a when they are in the diagnosis position, in the treatment position, and even being moved from the diagnosis position to the treatment position.

In addition, as shown in FIG. 5 and FIG. 8, the state of the treatment table 5 in the patient position of particle beam therapy and that in the 3D imaging diagnosis position are 180-degree rotationally symmetric about the central axis of the support leg 6a. Accordingly, the entire treatment table 5 is free from changes in the state such as deflection and deformation between the diagnosis position and the treatment position, and the lesion A can be positioned to the isocenter 8 of the particle beam therapy system highly accurately.

Note that such members (support leg 6a, member 4c) that do not move in the treatment table 5 are each configured to have a symmetric shape about the movement axis. In this case, the treatment table 5 is 180-degree rotationally symmetric about the central axis of the support leg 6a, and thus has a symmetric shape relative to the axis.

Embodiment 3

The arrangement of the diagnostic 3D imaging unit 16 is restricted by the shape or size of the particle beam therapy room, and thus described below is a case where the arrangement of the diagnostic 3D imaging unit 16 is different from that of each of above Embodiments 1 and 2.

In this Embodiment 3, the configuration of the respective components in the treatment table moving mechanism 4 is different from that of each of above Embodiment 1 and 2. However, the shape and operation of each component in the treatment table moving mechanism 4 are omitted for convenience. Instead, the movement of the treatment table 5 as a whole will be described with reference to FIG. 9(a) to FIG. 9(c).

Figure 9:
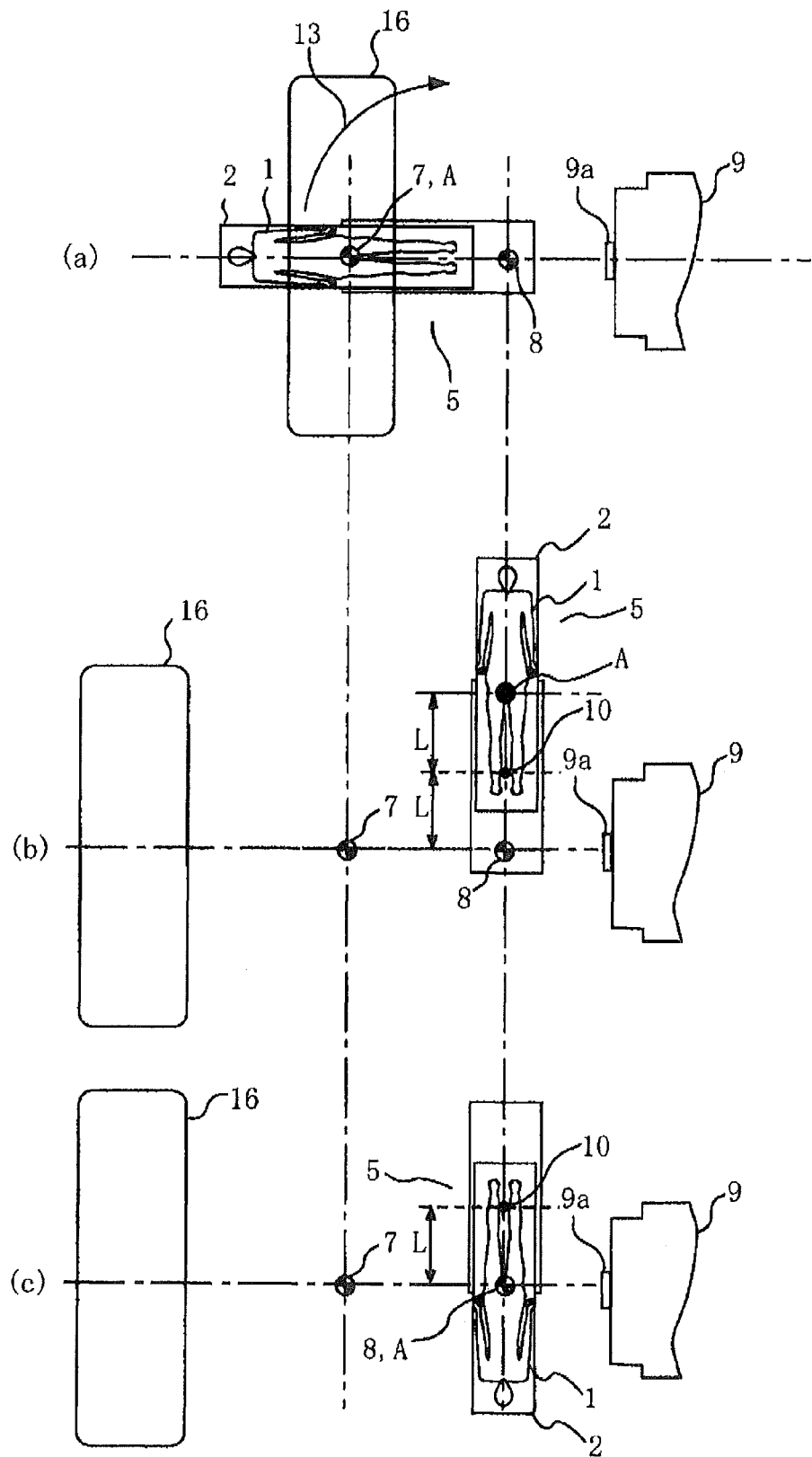
FIG. 9 is a diagram illustrating an operation of a treatment table moving mechanism of a treatment table system according to Embodiment 3 of the present invention.

Note that FIG. 9(a) is a top view of the treatment table 5 arranged in the 3D imaging diagnosis position, and FIG. 9(c) is a top view of the treatment table 5 arranged in the patient position of particle beam therapy. FIG. 9(b) illustrates a step of a procedure of moving the treatment table 5 from the 3D imaging diagnosis position to the patient position of particle beam therapy.

As shown in FIG. 9(a), the treatment table 5 is located in the diagnosis position in the diagnostic 3D imaging unit 16 arranged in a manner as to face the radiation port 9 emitting particle beams. In this case, the isocenter of the diagnostic 3D imaging unit 16 is set as the virtual isocenter 7 of the particle beam therapy system, and the lesion A is positioned to the virtual isocenter 7 by using the first and second lesion positioner systems 3 and 6 (6a).

The treatment table 5 is then turned clockwise 90 degrees, in the drawing, about the position of the isocenter 8 of the particle beam therapy system, which corresponds to the state shown in FIG. 9(b). When the treatment table 5 is to be moved, the diagnostic 3D imaging unit 16 is removed backward so as not to hinder the movement of the treatment table 5.

Next, in the same manner as above Embodiment 1, the treatment table 5 is turned 180 degrees about the rotation axis 10 passing through the midway point between the lesion A and the isocenter 8, which corresponds to the state shown in FIG. 9(c). Accordingly, the lesion A is moved and positioned to the isocenter 8 of the particle beam therapy system.

In this embodiment as well, the treatment table moving mechanism 4 not shown moves, in the same manner as in above Embodiments 1 and 2, the treatment table 5 to the treatment position relative to the particle beam therapy system while maintaining the states of the top board 2 and the lesion positioner system obtained at the time when the lesion A is positioned to the virtual isocenter 7. In addition, the state of the treatment table moving mechanism 4 at the time when the lesion A is moved to the position of the isocenter 8 of the particle beam therapy system is the same as the state thereof at the time when the lesion A is positioned to the virtual isocenter 7. Accordingly, in the same manner as in above Embodiments 1 and 2, the entire treatment table 5 is free from changes in the state such as deflection and deformation between the diagnosis position and the treatment position, and the lesion A can be positioned to the isocenter 8 of the particle beam therapy system highly accurately.

Figure 10:
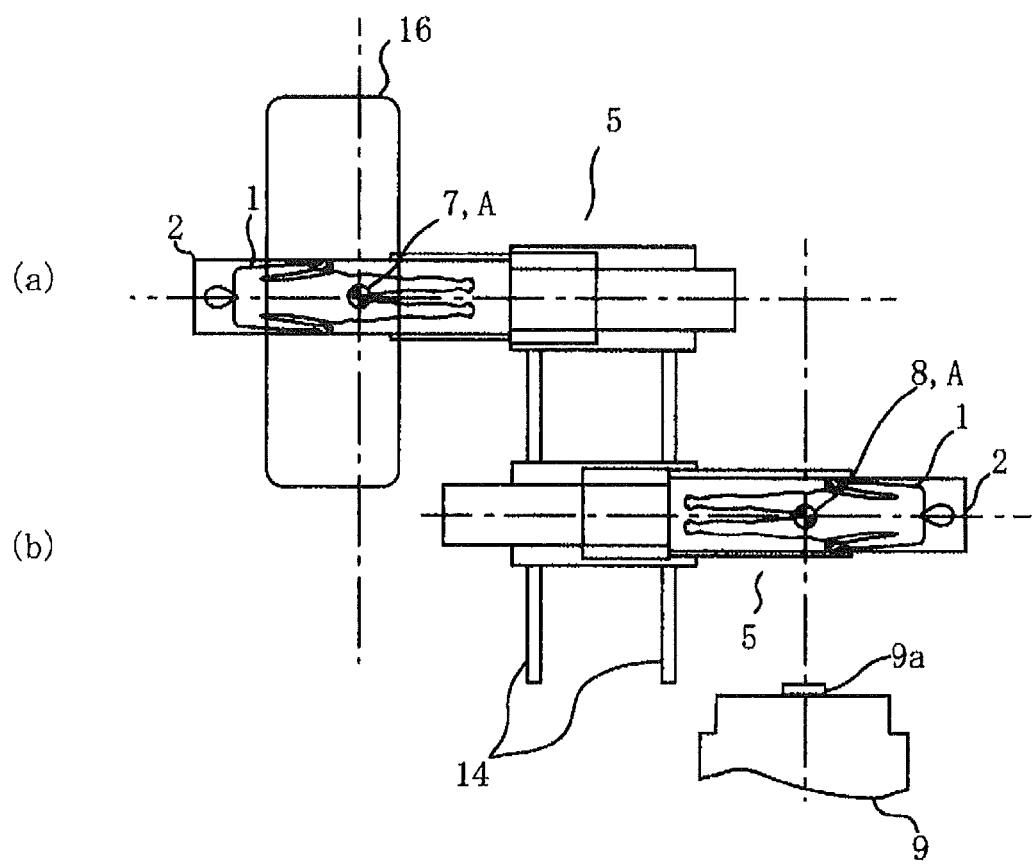
FIG. 10 is a diagram illustrating an operation of a treatment table moving mechanism of a treatment table system according to another example of Embodiment 3 of the present invention.

Note that, as shown in FIG. 10, a rail 14 may be laid on the floor of a treatment room so as to allow parallel displacement of the whole of the treatment table 1. In this case, after the treatment table is moved in the same manner as the case shown in FIG. 2, the treatment table 5 is subject to parallel displacement on the rail 14, and then moved to the treatment position relative to the particle beam therapy system.

In addition, in the above respective embodiments, the treatment table 5 is supported by the support leg 6 (6a) from below. However, the treatment table 5 may by supported by hanging from above. In this case as well, the treatment table moving mechanism 4 is located under the first lesion positioner system 3 and supports the first lesion positioner system 3 thereby to move the treatment table 5. Accordingly, in the same manner as in above Embodiments 1 and 2, the entire treatment table 5 is free from changes in the state such as deflection and deformation between the diagnosis position and the treatment position. Thus, the lesion A can be positioned to the isocenter 8 of the particle beam therapy system highly accurately.

In addition, in above Embodiments 1 to 3, after the lesion A is positioned to the virtual isocenter 7, the treatment table 5 is moved and positioned to the isocenter 8 of the particle beam therapy system. However, the lesion A may be positioned to the isocenter 8, based on the preceding positioning information. In this case, means for storing the positioning information of the lesion positioner systems 3 and 6 (6a) is provided, and the lesion A is positioned to the isocenter 8 by using the previously stored positioning information. Then, based on an image taken by an X-ray imaging device, which is a diagnostic apparatus normally arranged together with the particle beam therapy system, the position of the lesion A is corrected by using the lesion positioner systems 3 and 6 (6a). Accordingly, when the particle beam therapy is performed on a single lesion A of a subject 1 for a plurality of number of times, the lesion A can be positioned to the isocenter 8 easily, quickly, and highly accurately.

INDUSTRIAL APPLICABILITY

The present invention is applicable to a particle beam therapy system having a low degree of freedom in positioning the radiation port, for example, to a particle beam therapy system having a fixed radiation port or that of a gantry type in which a radiation port is movable only laterally.

The invention claimed is:

1. A treatment table system for a particle beam therapy system which employs 3D imaging diagnosis for particle beam therapy in which a lesion of a subject is irradiated with high energy charged particle beams emitted from an accelerator, the treatment table system comprising:
    a top board on which the subject is placed;
    a lesion positioner system which supports and moves the top board thereby to position the lesion to an isocenter of the particle beam therapy system; and
    a treatment table moving mechanism which moves a treatment table provided with the lesion positioner system and the top board between a diagnosis position in a diagnostic 3D imaging unit and a treatment position relative to the particle beam therapy system, wherein
    the lesion positioner system is configured with a plurality of hierarchically arranged members to move the top board based on a combination of any of movements in a longitudinal direction, a lateral direction, a vertical direction, a rotation direction about an axis along the longitudinal direction, and a rotation direction about an axis along the lateral direction,
    when the treatment table is in the diagnosis position in the diagnostic 3D imaging unit, the lesion positioner system sets an isocenter of the diagnostic 3D imaging unit as a virtual isocenter of the particle beam therapy system, and positions the lesion to the virtual isocenter, based on an image of the lesion obtained by the diagnostic 3D imaging unit, in consideration of particle beam therapy based on a position of a particle radiation port and a direction of particle radiation of the particle beam therapy system,
    the treatment table moving mechanism includes a plurality of members which are driven independently from one another in respective predetermined directions to perform rotational movement or translational movement, and
    the treatment table moving mechanism moves the top board and the lesion positioner system translationally such that a central portion of the top board approaches a rotational axis of the treatment table moving mechanism in order to reduce the radius of the rotation of the top board, rotates the top board and the lesion positioner system, and translationally moves the top board and the lesion positioner system to the treatment position relative to the particle beam therapy system, while maintaining states of the top board and the lesion positioner system at a time of positioning when the lesion is positioned to the virtual isocenter, thereby to position the lesion to the isocenter of the particle beam therapy system.

2. The treatment table system according to claim 1, further comprising:
    means for setting the virtual isocenter within a coverage of diagnosis performed by the diagnostic 3D imaging unit, wherein
    the image of the lesion is an image of diagnosis which is performed by moving the isocenter of the diagnostic 3D imaging unit so as to coincide with the virtual isocenter.

3. The treatment table system according to claim 1, wherein
    the lesion positioner system:
    allows the lesion to be positioned to the isocenter of the particle beam therapy system, based on the image of the lesion obtained by an X-ray imaging device;
    includes means for maintaining positioning information of the lesion positioner system; and
    under a state where the treatment table is in the treatment position relative to the particle beam therapy system, corrects the position of the lesion, based on the image of the lesion obtained by the X-ray imaging device after the lesion is positioned to the isocenter of the particle beam therapy system, based on the maintained positioning information.

* * * * *